(12) United States Patent
Lu et al.

(10) Patent No.: US 10,070,870 B2
(45) Date of Patent: Sep. 11, 2018

(54) MEDICAL DRILL BIT

(71) Applicant: NATIONAL PINGTUNG UNIVERSITY OF SCIENCE & TECHNOLOGY, Pingtung County (TW)

(72) Inventors: Wei-Hua Lu, Pingtung County (TW); Yung-Chuan Chen, Kaohsiung (TW)

(73) Assignee: NATIONAL PINGTUNG UNIVERSITY OF SCIENCE & TECHNOLOGY, Pingtung County (TW)

( * ) Notice: Subject to any disclaimer, the term of this patent is extended or adjusted under 35 U.S.C. 154(b) by 229 days.

(21) Appl. No.: 15/149,331

(22) Filed: May 9, 2016

(65) Prior Publication Data

US 2017/0319218 A1    Nov. 9, 2017

(51) Int. Cl.
| A61B 17/16 | (2006.01) |
| A61C 3/02 | (2006.01) |
| A61C 8/00 | (2006.01) |
| A61B 17/32 | (2006.01) |
| B23B 51/06 | (2006.01) |
| B23B 51/04 | (2006.01) |

(52) U.S. Cl.
CPC .......... *A61B 17/1617* (2013.01); *A61B 17/16* (2013.01); *A61B 17/1613* (2013.01); *A61B 17/1615* (2013.01); *A61B 17/1644* (2013.01); *A61B 17/32* (2013.01); *A61C 3/02* (2013.01); *A61C 8/0089* (2013.01); *A61B 2017/1651* (2013.01); *B23B 51/042* (2013.01); *B23B 51/06* (2013.01)

(58) Field of Classification Search
CPC . A61B 17/16; A61B 17/1613; A61B 17/1615; A61B 17/1617; A61B 17/1644; A61B 2017/1651; A61C 3/02; B23B 51/042; B23B 51/06
See application file for complete search history.

(56) References Cited

U.S. PATENT DOCUMENTS 5,078,605 A * 1/1992 Sutter ................ A61B 17/1644
408/59
2017/0173706 A1 * 6/2017 Georgiou ........... B23Q 11/1015

FOREIGN PATENT DOCUMENTS

EP        2364668 B1    11/2013
TW     201617040 A *    5/2016

OTHER PUBLICATIONS

Taiwanese Office Action dated Jan. 6, 2016 for Taiwanese Patent Application No. 103139136, 5 pages.

* cited by examiner

*Primary Examiner* — Larry E Waggle, Jr.
(74) *Attorney, Agent, or Firm* — Jackson IPG PLLC; Demian K. Jackson

(57) ABSTRACT

A medical drill bit comprises an accommodating slot disposed concavely on a main body of the medical drill bit, a separate board disposed in the accommodating slot to separate the accommodating slot into a first slot and a second slot, and a lid engaging with the separate board and covering the accommodating slot. The lid and the separate board do not rotate with the main body when the main body in rotation. The accommodating uses to fill with cooling liquid which able to be pumped out from the accommodating slot, and fresh cooling liquid is able to inject into the accommodating slot for cooling the drill bit in rotation.

7 Claims, 6 Drawing Sheets

MEDICAL DRILL BIT

FIELD OF THE INVENTION

The present invention relates to a medical drill bit applicable for tooth implantation or bone surgery, particularly relates to a medical drill bit enable to prevent bone necrosis or tissue destruction caused by frictional heat produced by friction between the drill bit and bone during tooth implantation or bone surgery.

BACKGROUND OF THE INVENTION

With reference to FIG. 6, tooth implantation or bone surgery usually uses a drill bit 10 to drill through a bone (e.g., alveolar bone) 20 to form a fixation hole 21 applied for implantation of bone nail or tooth nail (tooth implant). Friction temperature of the drill bit 10 and the bone 20 will increase with rotary speed of the drill bit 10 and depth of the fixation hole 21, and heat produced by drilling will cause bone necrosis at contacting site of the bone (e.g., alveolar bone) and the bone nail or tooth nail (tooth implant), so a nozzle 30 is used to apply a cooling liquid 40 spraying to the drill bit 10 and the bone 20 for decreasing high temperature caused by friction of the drill bit 10 and the bone 20 in prior art. However, the cooling liquid 40 does not easily permeate into the fixation hole 21 for cooling after the drill bit 10 drill into the bone 20, conventional outer cooling process using the nozzle 30 spraying the cooling liquids 40 may still cause tissue destruction of the bone 20 to decrease fixing strength of bone nail or tooth nail (tooth implant) in the bone 20, and may cause bone necrosis.

SUMMARY

The primary object of the present invention is to provide a medical drill bit comprising an accommodating slot disposed concavely on a main body of the medical drill bit, and comprising a separate board disposed in the accommodating slot to separate the accommodating slot into a first slot and a second slot. The separate board engages with a lid which covers the accommodating slot. The lid and the separate board do not rotate with the main body when the main body is in rotation. The accommodating slot enables to fill with cooling liquid which able to be pumped out from the accommodating slot, and fresh cooling liquid is able to be injected into the accommodating slot for cooling the medical drill bit.

A medical drill bit of the present invention includes a main body, a separate board and a lid, wherein the main body comprises a top portion, a ring wall and an accommodating slot disposed concavely on the top portion, the accommodating slot comprises an opening on the top portion, an inner surface of the ring wall surrounds the accommodating slot, and a cutting slot is disposed on an outer surface of the ring wall; the separate board is disposed in the accommodating slot to separate the accommodating slot into a first slot and a second slot communicating with the second slot, wherein the separate board comprises a head portion and a board portion connecting with the head portion, the head portion comprises a liquid inlet communicating with the first slot and a liquid outlet communicating with the second slot, and a edge of the separate board does not contact with the inner surface of the ring wall; the lid covers the opening of the accommodating slot and engages with the separate board to seal the liquid inlet and the liquid outlet, wherein the lid and the separate board do not rotate with the main body when the main body is in rotation.

The cooling liquid in the accommodating slot is able to be pumped out and inject again, so heat exchange between the cooling liquid flowing in the accommodating slot and the main body of the drill bit enables to decrease the heat produced when the drill bit drills into a bone.

DETAILED DESCRIPTION OF THE INVENTION

Figure 1:
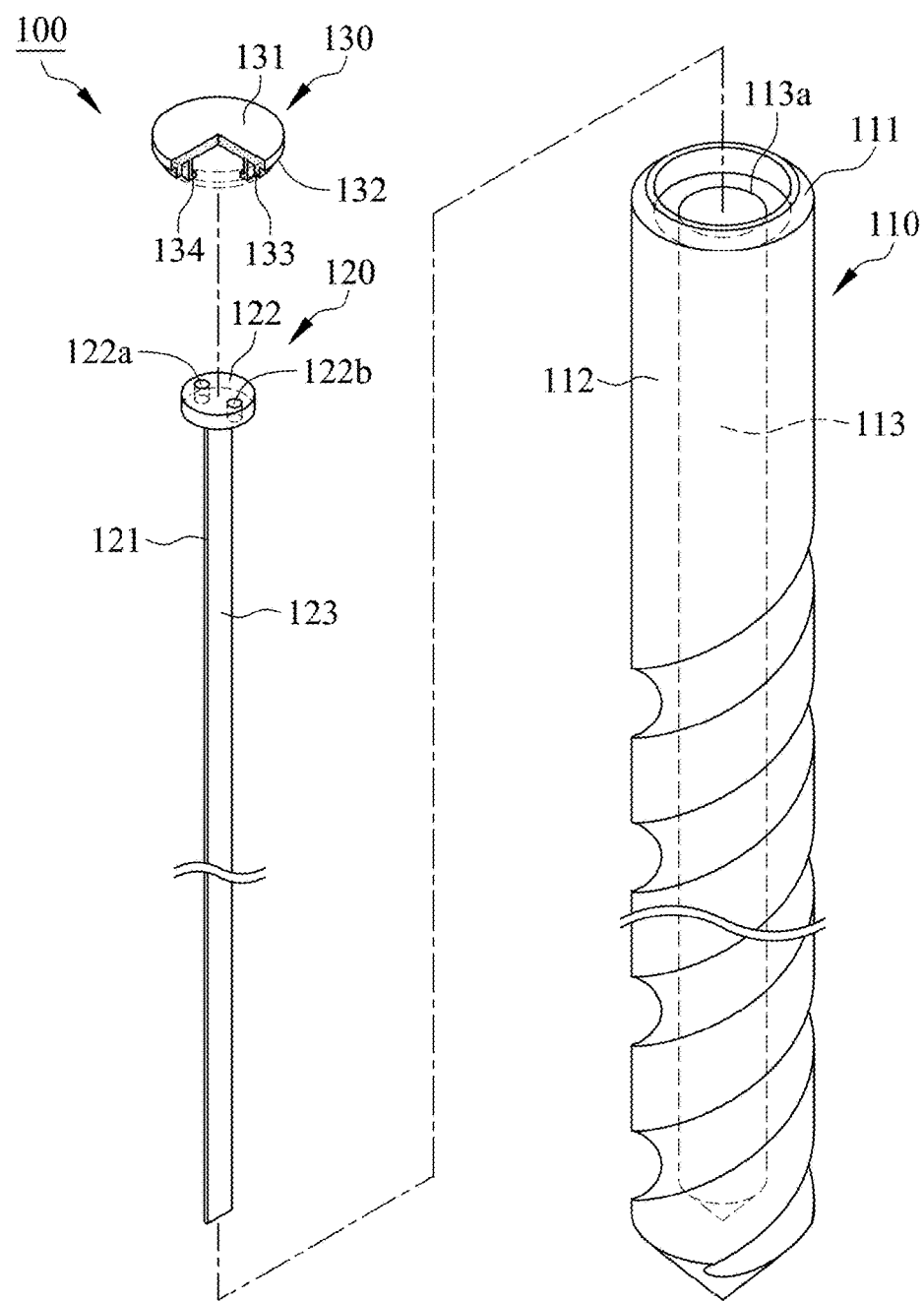
FIG. 1 is a perspective exploded diagram illustrating a medical drill bit in accordance with the present invention.
Figure 2:
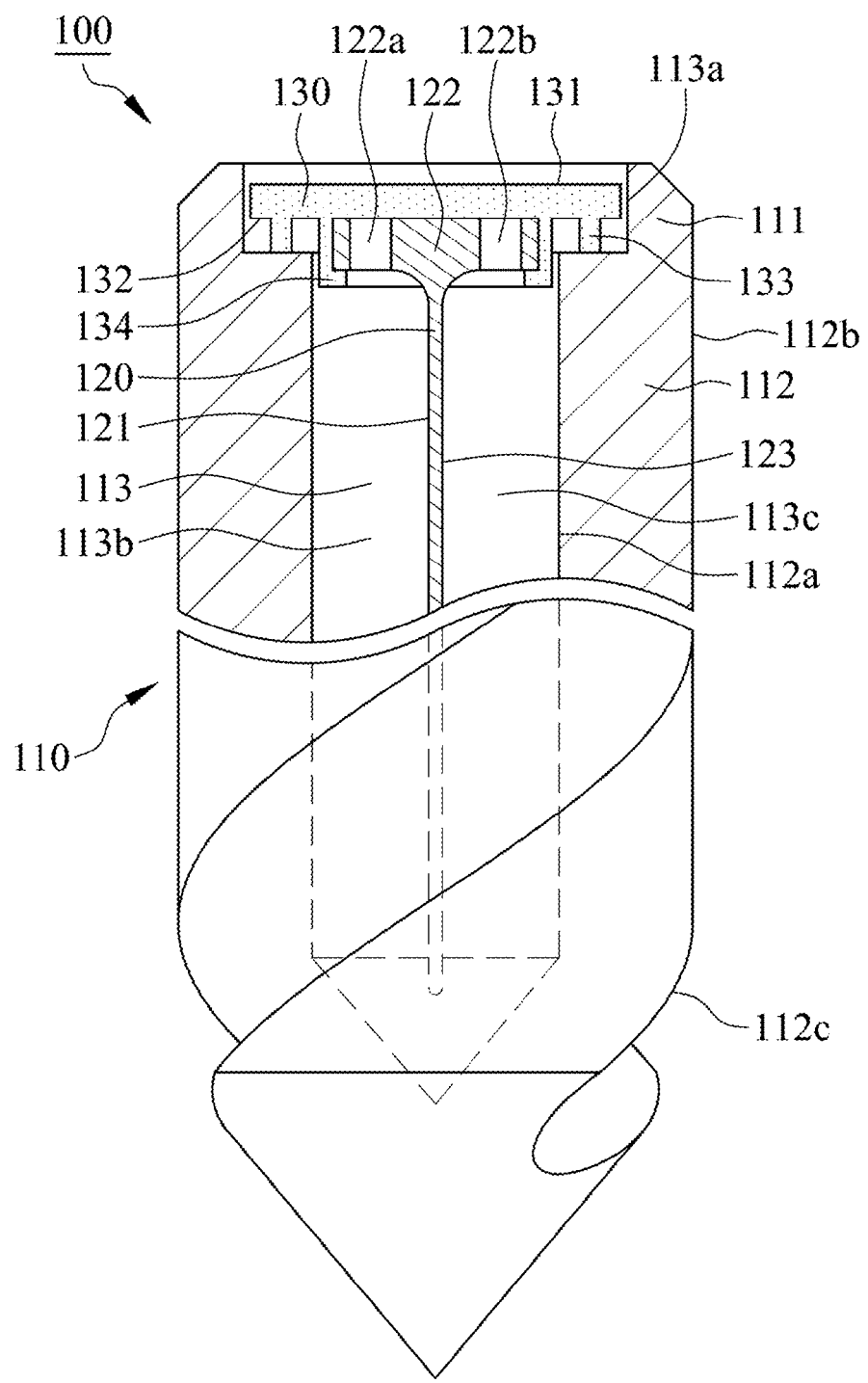
FIG. 2 is a section view diagram illustrating the medical drill bit in accordance with the present invention.
Figure 3:
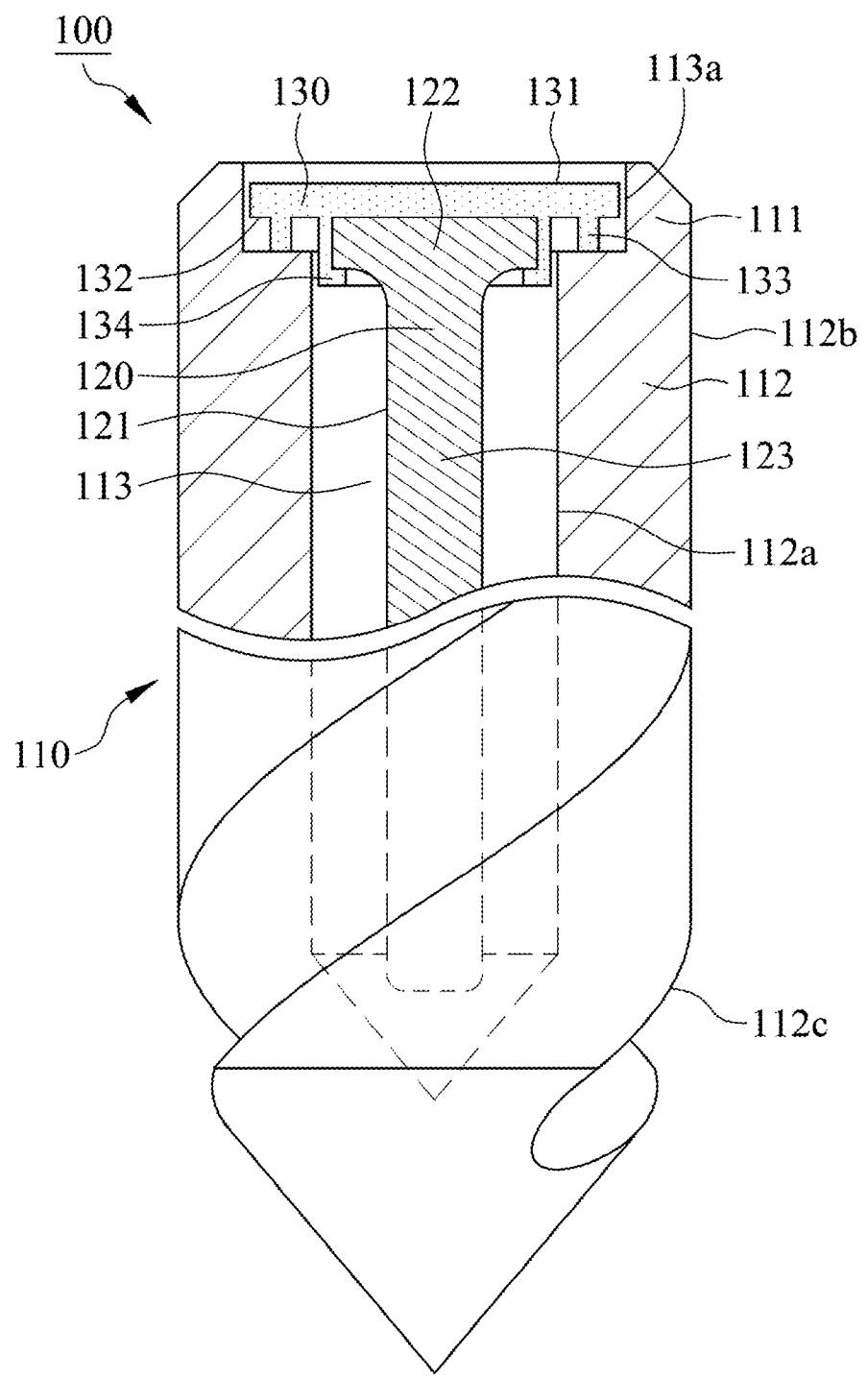
FIG. 3 is a section view diagram illustrating the medical drill bit in accordance with the present invention.

With reference to FIGS. 1, 2 and 3, a medical drill bit 100 in accordance with an embodiment of the present invention includes a main body 100, a separate board 110, a separate board 120 and a lid 130, wherein the main body 110 has a top portion 111, a ring wall 112 and an accommodating slot 113. The accommodating slot 113 is disposed concavely on the top portion 111 and comprises an opening 113a on the top portion 111. An inner surface 112a of the ring wall 112 surrounds the accommodating slot 113, and a cutting slot 112c is disposed concavely on an outer surface 112b of the ring wall 112.

With reference to FIGS. 1, 2 and 3, the separate board 120 is disposed in the accommodating slot 113 to separate the accommodating slot 113 into a first slot 113b and a second slot 113c, wherein the first slot 113b communicates with the second slot 113c. With reference to FIG. 3, an edge 121 of the separate board 120 does not contact with the inner surface 112a of the ring wall 112. In this embodiment, the separate board 120 comprises a head portion 122 and a board portion 123 connecting with the head portion 122, wherein the head portion 122 comprises a liquid inlet 122a and a liquid outlet 112b. With reference to FIG. 2, the liquid inlet 112a communicates with the first slot 113b, and the liquid outlet 112b communicates with the second slot 113c.

With reference to FIGS. 1, 2 and 3, the lid 130 engages with the separate board 120 and covers the opening 113a of the accommodating slot 113. The lid 130 comprises a top surface 131 and a bottom surface 132, wherein the head portion 122 of the separate board 120 connects to the bottom surface 132 of the lid 130. In this embodiment, the lid 130 further comprises an engaging base 134 disposing on the bottom surface 132, wherein the head portion 122 of the separate board 120 engages with the engaging base 134 of the lid 130 to make the lid 130 integrate together with the separate board 120 to seal the liquid inlet 122a and the liquid outlet 122b. In addition, the lid 130 enables to be formed as one piece with the separate board 120 in other embodiment to make the head portion 122 of the separate board 120 integrates with the bottom surface 132 of the lid 130 directly.

With reference to FIGS. 1, 2 and 3, the lid 130 further comprises a sealing ring 133 disposed on the bottom surface 132. In this embodiment, the sealing ring 133 locates outside of the engaging base 134 and contacts with the top portion 111 of the main body 110 slightly to make the accommodating slot 113 become a space able to accommodate cooling liquid.

Figure 4:
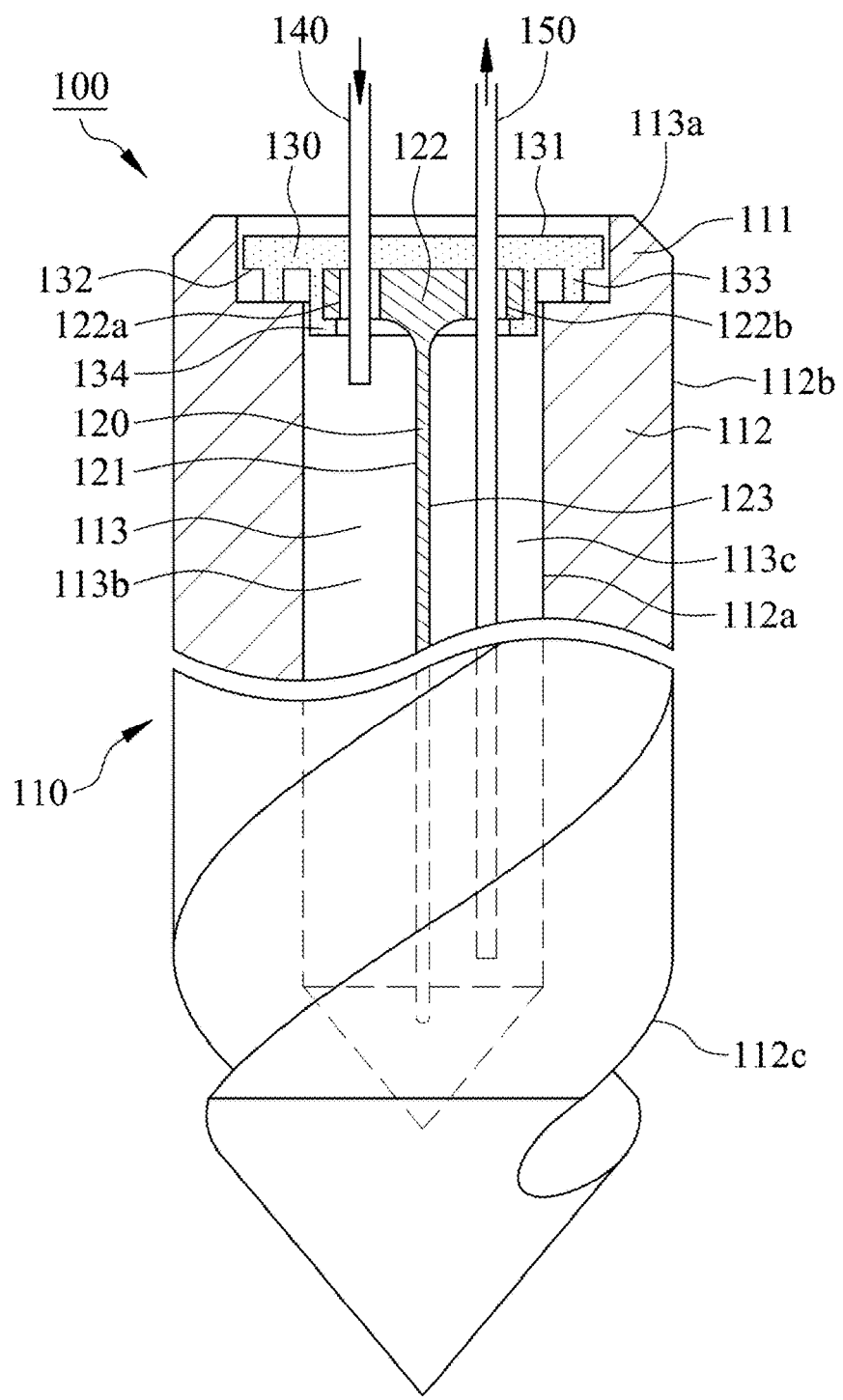
FIG. 4 is a section view diagram illustrating the medical drill bit in accordance with the present invention.

With reference to FIG. 4, the medical drill bit 100 further includes an inlet tube 140 and an outlet tube 150 which penetrate through the lid 130 respectively, wherein the inlet tube 140 communicates with the first slot 113b via the liquid inlet 122a, and the outlet tube 150 communicates with the second slot 113c via the liquid outlet 122b.

Figure 5:
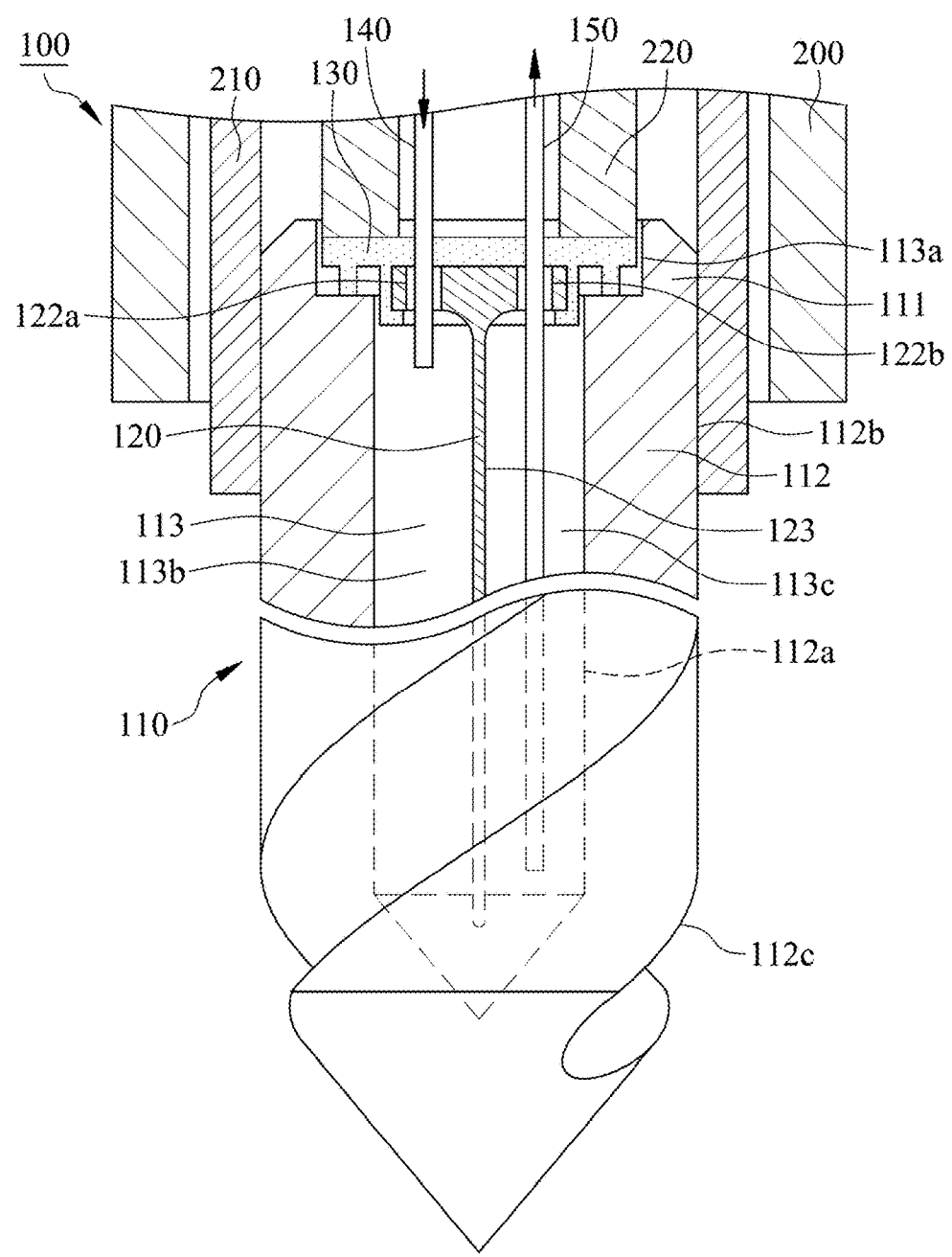
FIG. 5 is a section view diagram illustrating the medical drill bit in using state in accordance with the present invention.
Figure 6:
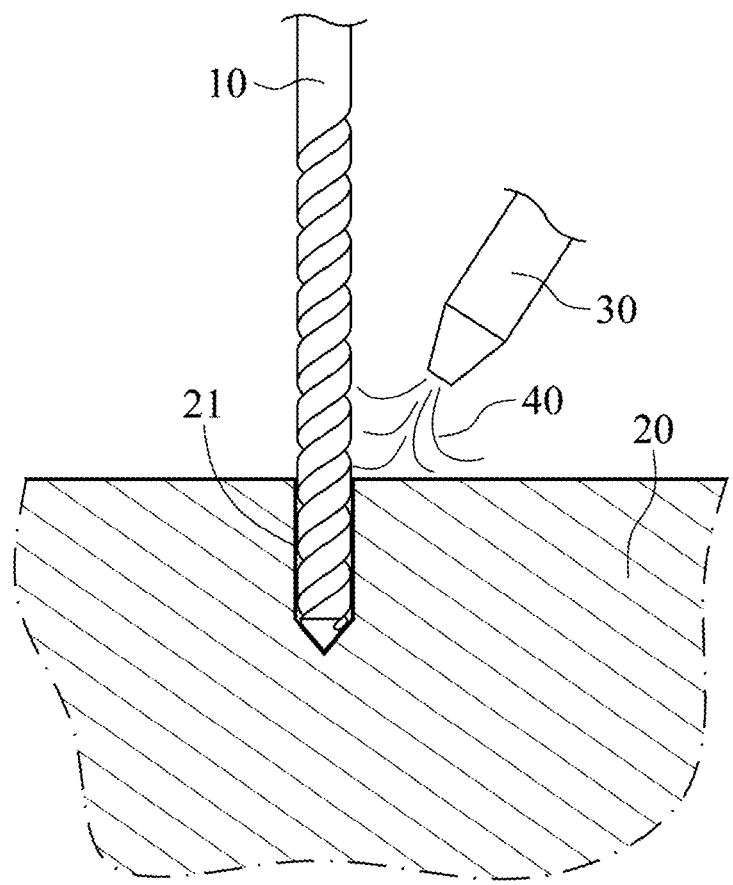
FIG. 6 is a diagram illustrating the conventional drill bit drill through bone.

With reference to FIG. 5, the medical drill bit 100 is disposed on a fixture 210 of a handle 200 and the lid 130 is disposed on a fixing base 220 of the handle 200, wherein a motor enables to drive the fixture 210 in rotation. Owing to the sealing ring 133 contacts with the top portion 111 of the main body 110 slightly, the lid 130, the separate board 120, the inlet tube 140 and the outlet tube 150 do not rotate with the main body 110 when the fixture 210 drives the main body 110 of the medical drill bit 100 in rotation.

With reference to FIG. 5, a cooling liquid is filled in the accommodating slot 113 via the inlet tube 140, and the cooling liquid in the accommodating slot 113 is able to be pumped out via the outlet tube 150. The cooling liquid flowing circularly in the accommodating slot 113 by the inlet tube 140 and the outlet tube 150 exchanges the heat produced by the main body 110 of the medical drill bit 100 to reduce high temperature caused by friction of bone and the main body 110 of the medical drill bit 100. Preferably, the cooling liquid can spray outside of the main body 110 of the medical drill bit 100 when using the medical drill bit 100 of the present invention to drill bone.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A medical drill bit including:
   a main body having a top portion, a ring wall and an accommodating slot disposed concavely on the top portion, wherein the accommodating slot comprises an opening on the top portion, an inner surface of the ring wall surrounds the accommodating slot and a cutting slot is disposed concavely on an outer surface of the ring wall;
   a separate board disposed in the accommodating slot to separate the accommodating slot into a first slot and a second slot communicating with the first slot, wherein the separate board comprises a head portion and a board portion connecting with the head portion, the head portion comprises a liquid inlet communicating with the first slot and comprises a liquid outlet communicating with the second slot, and an edge of the separate board does not contact with the inner surface of the ring wall; and
   a lid covering the opening of the accommodating slot and engaging with the separate board to seal the liquid inlet and the liquid outlet, wherein the lid and the separate board do not rotate with the main body when the main body is in rotation.

2. The medical drill bit in accordance with claim 1, wherein the lid comprises a top surface, a bottom surface and a sealing ring disposed on the bottom surface, and wherein the sealing ring contacts with the top portion of the main body.

3. The medical drill bit in accordance with claim 1, wherein the lid comprises a top surface, a bottom surface and an engaging base disposed on the bottom surface, and wherein the head portion of the separate board engages with the engaging base of the lid.

4. The medical drill bit in accordance with claim 1 further includes an inlet tube and an outlet tube penetrating through the lid respectively, wherein the inlet tube communicates with the first slot via the liquid inlet and the outlet tube communicates with the second slot via the liquid outlet.

5. The medical drill bit in accordance with claim 1, wherein the lid is formed as one piece with the separate board.

6. The medical drill bit in accordance with claim 5, wherein the head portion of the separate integrates with a bottom surface of the lid.

7. A medical drill bit including:
   a main body having a top portion, a ring wall and an accommodating slot disposed concavely on the top portion, wherein the accommodating slot comprises an opening on the top portion, an inner surface of the ring wall surrounds the accommodating slot and a cutting slot is disposed concavely on an outer surface of the ring wall;
   a lid covering the opening of the accommodating slot, wherein the lid comprises a top surface, a bottom surface and a sealing ring disposed on the bottom surface, the sealing ring contacts with the top portion of the main body, and the lid does not rotate with the main body when the main body is in rotation; and
   an inlet tube and an outlet tube, wherein the inlet tube and the outlet tube penetrate through the lid respectively to communicate with the accommodating slot, and the inlet tube and the outlet tube do not rotate with the main body.

* * * * *